United States Patent
Sueda et al.

(10) Patent No.: US 9,487,409 B2
(45) Date of Patent: Nov. 8, 2016

(54) SPHERICAL ZINC OXIDE PARTICLE CONSISTING OF INTEGRATED PLATE-LIKE PARTICLES, METHOD FOR PRODUCING THE SAME, COSMETIC, AND THERMAL CONDUCTIVE FILLER

(71) Applicant: Sakai Chemical Industry Co., Ltd., Sakai-shi, Osaka (JP)

(72) Inventors: Satoru Sueda, Iwaki (JP); Mitsuo Hashimoto, Iwaki (JP); Atsuki Terabe, Iwaki (JP); Koichiro Magara, Iwaki (JP)

(73) Assignee: SAKAI CHEMICAL INDUSTRY CO., LTD, Osaka (JP)

( * ) Notice: Subject to any disclaimer, the term of this patent is extended or adjusted under 35 U.S.C. 154(b) by 0 days.

(21) Appl. No.: 14/376,672

(22) PCT Filed: Mar. 8, 2013

(86) PCT No.: PCT/JP2013/056462
§ 371 (c)(1),
(2) Date: Aug. 5, 2014

(87) PCT Pub. No.: WO2013/133412
PCT Pub. Date: Sep. 12, 2013

(65) Prior Publication Data
US 2015/0050496 A1     Feb. 19, 2015

(30) Foreign Application Priority Data
Mar. 8, 2012     (JP) .................................. 2012-051789

(51) Int. Cl.
*C01G 9/02*     (2006.01)
*B32B 5/16*     (2006.01)
(Continued)

(52) U.S. Cl.
CPC ................. *C01G 9/02* (2013.01); *A61K 8/025* (2013.01); *A61K 8/27* (2013.01); *A61Q 17/04* (2013.01); *B82Y 30/00* (2013.01); *C09C 1/043* (2013.01);
(Continued)

(58) Field of Classification Search
CPC ............ C01P 2004/01; C01P 2004/32; C01P 2004/51; C01P 2004/62; C01P 2006/12
USPC ............................ 423/99, 622, 275; 428/402
See application file for complete search history.

(56) References Cited

U.S. PATENT DOCUMENTS

2010/0104871 A1     4/2010   Hashimoto et al.
2011/0244236 A2*   10/2011  Sueda et al. .................. 428/402

FOREIGN PATENT DOCUMENTS

JP     H11-49516 A     2/1999
JP     2004-115325 A   4/2004
(Continued)

OTHER PUBLICATIONS

Khan et al., "Low temperature synthesis of fluorescent ZnO nanoparticles", Applied Surface Science, 257 (2010) 1756-1761.
(Continued)

*Primary Examiner* — Holly Le
(74) *Attorney, Agent, or Firm* — Polsinelli PC

(57) ABSTRACT

The present disclosure provides spherical zinc oxide particles consisting of integrated plate-like particles which can be used as a cosmetic raw material, a thermal conductive filler and the like, and a method for production of the same. Spherical zinc oxide particles consisting of integrated plate-like particles, which have a median size of 0.01 μm or more and a D90/D10 in particle size distribution of 5.0 or less are provided.

19 Claims, 5 Drawing Sheets

(51) Int. Cl.
  *A61K 8/27* (2006.01)
  *A61Q 17/04* (2006.01)
  *C09C 1/04* (2006.01)
  *A61K 8/02* (2006.01)
  *B82Y 30/00* (2011.01)
  *C09K 5/14* (2006.01)

(52) U.S. Cl.
  CPC ........... *C09K 5/14* (2013.01); *A61K 2800/412* (2013.01); *A61K 2800/60* (2013.01); *C01P 2002/72* (2013.01); *C01P 2002/74* (2013.01); *C01P 2004/01* (2013.01); *C01P 2004/03* (2013.01); *C01P 2004/32* (2013.01); *C01P 2004/51* (2013.01); *C01P 2004/61* (2013.01); *C01P 2004/62* (2013.01); *C01P 2004/64* (2013.01); *C01P 2006/12* (2013.01); *C01P 2006/32* (2013.01); *C01P 2006/60* (2013.01); *Y10T 428/2982* (2015.01)

(56) References Cited

FOREIGN PATENT DOCUMENTS

| | | |
|---|---|---|
| JP | 2004142999 A | 5/2004 |
| JP | 2008-254989 A | 10/2008 |
| JP | 2008-254990 A | 10/2008 |
| JP | 2008-254991 A | 10/2008 |
| JP | 2008-254993 A | 10/2008 |
| JP | 2008-254994 A | 10/2008 |
| JP | 2009-249226 A | 10/2009 |

OTHER PUBLICATIONS

Umar et al., "Large-scale synthesis of ZnO balls made of fluffy thin nanosheets by simple solution process: Structural, optical and photocatalytic properties", Journal of Colloid and Interface Science, 363 (2011) 521-528.

* cited by examiner

SPHERICAL ZINC OXIDE PARTICLE CONSISTING OF INTEGRATED PLATE-LIKE PARTICLES, METHOD FOR PRODUCING THE SAME, COSMETIC, AND THERMAL CONDUCTIVE FILLER

CROSS REFERENCE TO RELATED APPLICATIONS

This application is a National Phase filing under 35 U.S.C. §371 of PCT/JP2013/056462 filed on Mar. 8, 2013; and this application claims priority to Application No. 2013-051789 filed in Japan on Mar. 8, 2012; the entire contents of which is hereby incorporated by reference.

TECHNICAL FIELD

The present disclosure relates to a spherical zinc oxide particle consisting of integrated plate-like particles, a method for producing the same, a cosmetic, and a thermal conductive filler.

BACKGROUND OF THE DISCLOSURE

Zinc oxide particles, which have been used as a sunscreen ultraviolet blocking agent in cosmetic product applications, are ultrafine particles having an average particle diameter of 100 nm or less. However, such zinc oxide ultrafine particles for ultraviolet blocking deteriorate slippage, and are therefore hardly used for foundations. Therefore, plate-shaped particles such as those of talc, mica and barium sulfate are generally contained to provide slippage. However, these plate-shaped particles do not have an ultraviolet blocking effect, and therefore for imparting ultraviolet blocking performance, zinc oxide fine particles or titanium oxide fine particles in an amount small enough that slippage is not hindered, or an organic ultraviolet absorbing agent must be used in combination.

In addition, as a burr-like zinc oxide consisting of integrated needle-like particles, particles disclosed in Patent Documents 1 and 2 are publicly known. As an urchin-like zinc oxide particle consisting of integrated needle-like particles, particle disclosed in Patent Document 3 is publicly known. However, these zinc oxide particles consist of integrated needle-like particles not plate-like particles. In addition, a particle disclosed in Patent Document 4 is publicly known as aegagropila-shaped particles consisting of integrated plate-like particles. However, the particles have an uneven particle diameter, and the particle size distribution thereof is not sharp.

Further, spherical zinc oxides disclosed in Patent Documents 5 to 8 are publicly known. However, the particles are not spherical zinc oxide particles consisting of integrated plate-like particles. Zinc oxide particles of the present disclosure are spherical zinc oxide particles consisting of integrated plate-like particles having a good slippage, a superior soft focus effect (a so called effect of blurring a base), and an ultraviolet blocking property. In the conventional technique, zinc oxide particles having three performances of a good slippage, a superior soft focus effect, a superior ultraviolet blocking property equal to that of ultrafine zinc oxide particles have been previously unknown.

PRIOR TECHNICAL DOCUMENTS

Patent Documents

[Patent Document 1] Japanese Kokai Publication 2008-254989
[Patent Document 2] Japanese Kokai Publication 2008-254991
[Patent Document 3] Japanese Kokai Publication 2004-115325
[Patent Document 4] Japanese Kokai Publication 2008-254990
[Patent Document 5] Japanese Kokai Publication Hei6-24743
[Patent Document 6] Japanese Kokai Publication 2004-142999
[Patent Document 7] Japanese Kokai Publication Hei11-49516
[Patent Document 8] Japanese Kokai Publication 2009-249226

SUMMARY OF INVENTION

Problems to be Solved by the Invention

In view of the situations described above, it is an object of the present disclosure to provide spherical zinc oxide particles consisting of integrated plate-like particles which can be used as a cosmetic raw material, a thermal conductive filler and the like, and a method for production of the same.

Means for Solving Object

The present disclosure relates to spherical zinc oxide particles consisting of integrated plate-like particles, which have a median size of 0.01 μm or more and a D90/D10 in particle size distribution of 5.0 or less.

The spherical zinc oxide particle consisting of integrated plate-like particles mentioned above is preferably obtained by a method comprising a step (1) of neutralizing a zinc salt aqueous solution by an alkali aqueous solution wherein said step (1) is performed in the presence of a hydrophilic dispersant.

The spherical zinc oxide particles consisting of integrated plate-like particles mentioned above preferably have a MIU (average friction coefficient) of 1.0 or less.

The present disclosure relates to a method for producing the spherical zinc oxide particle consisting of integrated plate-like particles mentioned above, which comprises a step (1) of neutralizing a zinc salt aqueous solution by an alkali aqueous solution wherein said step (1) is performed in the presence of a hydrophilic dispersant.

The present disclosure relates to a cosmetic comprising the spherical zinc oxide particle consisting of integrated plate-like particles mentioned above.

The present disclosure relates to a thermal conductive filler comprising the spherical zinc oxide particle consisting of integrated plate-like particles mentioned above.

Effects of the Invention

The spherical zinc oxide particle consisting of integrated plate-like particles of the present disclosure is suitable for cosmetics because of a good slippage and a superior soft focus effect.

In addition, the shape of above-mentioned particles consist of assembled many particles and it is expected to improve the thermal conductive performance between particles, so the superior performance as a thermal conductive filler is expected.

DETAILED DESCRIPTION OF PREFERRED EMBODIMENTS

Figure 1:
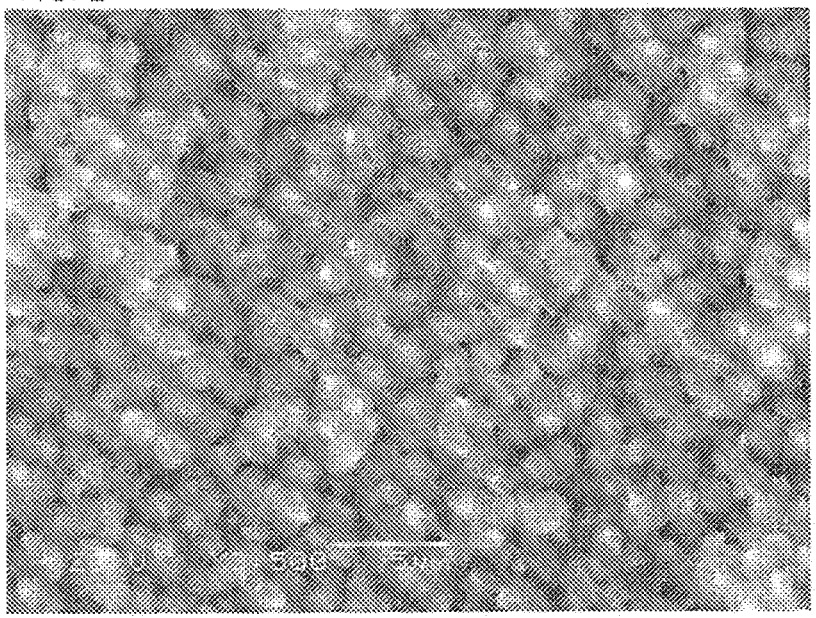
FIG. 1 is a scanning electron microscope photograph of zinc oxide particles obtained in Example 1.

The spherical zinc oxide particles consisting of integrated plate-like particles of the present disclosure have a spherical shape as a whole consisting of integrated plate-like particles as a sphere, and have a sharp particle size distribution. The present disclosure is completed by finding that in addition to an ultraviolet blocking effect of zinc oxide, a superior soft focus effect, and good powder touch are caused by the specific shape and the sharp particle size distribution.

The spherical zinc oxide particles consisting of integrated plate-like particles of the present disclosure have a median size of 0.01 μm or more. Particles having good performances such as slippage and thermal conductive property can be obtained by setting the particle diameter within the range. The median size is more preferably 0.05 μm or more, still more preferably 0.1 μm or more, and especially preferably 0.2 μm or more. The upper limit of the median size is not particularly limited but preferably 100 μm or less, more preferably 50 μm or less, still more preferably 20 μm or less, especially preferably 10 μm or less.

In the specification, when a powder is divided by particle diameter based on the median size into two groups, bigger group and smaller group have equal amounts. The median size is measured by laser diffraction/scattering particle size distribution analyzer LA-750 (manufactured by HORIBA, Ltd.).

The spherical zinc oxide particles consisting of integrated plate-like particles of the present disclosure are obtained by integrating plate-like particles not needle-like particles as a sphere. Such particle consisting of integrated plate-like particles has performances such as low friction, high thermal conductive property and so on, therefore can be used suitably for a cosmetic additive and a thermal conductive filler.

It becomes clear that the zinc oxide particle of the present disclosure consist of integrated plate-like particles by confirming that the (002) plane in the plate-like direction develops with the use of X-ray diffraction. When the obtained particle consist of integrated needle-like particles, the measurement result of x-ray diffraction is different.

In the zinc oxide particles of the present disclosure, the ratio of I(002)/I(100) is preferably 0.8 or more, wherein I(002) is the peak strength in a plate-like plane direction and I(100) is the peak strength in a column-like plane direction of zinc oxide in the x-ray diffraction.

The spherical zinc oxide particles consisting of integrated plate-like particles of the present disclosure have D90/D10 of 5.0 or less. D10 and D90 are values determined by measuring the particle size distribution. D10 means 10% cumulative particle diameter on volume basis and D90 means 90% cumulative particle diameter on volume basis. These values are measured by the same method as the median size. The D90/D10 is more preferably 4.5 or less. The spherical zinc oxide particles consisting of integrated plate-like particles having D90/D10 of 5.0 or less is preferred because contact points and adhesive property between fillers are increased when used as a thermal conductive filler, hereby the particles can generate a thermal conductive percolation and exert a superior thermal conductive performance even when filling amount is small.

The spherical zinc oxide particles consisting of integrated plate-like particles of the present disclosure preferably have a MIU (average friction coefficient) of 1.0 or less. In the specification, the MIU (average friction coefficient) is measured by following the method described in detail in Example. Zinc oxide particle having a MIU (average friction coefficient) more than 1.0 is inferior in the touch because the slippage is deteriorated when used in cosmetics. The MIU (average friction coefficient) is more preferably 0.8 or less.

The zinc oxide particles of the present disclosure preferably have a MMD (mean deviation of friction coefficient) of 0.02 or less. In the specification, the MMD (mean deviation of friction coefficient) is measured by following the method described in detail in this specification. The zinc oxide particles having a MMD (mean deviation of friction coefficient) more than 0.02 are inferior in the touch because a surface roughness generates when added in cosmetics. The MMD (mean deviation of friction coefficient) is more preferably 0.015 or less.

The zinc oxide particles of the present disclosure preferably have a BET specific surface area of 10 $m^2/g$ or more. By adjusting the BET specific surface area thereof within the range, the particles have especially suitable performances in effects including an antibacterial property and an astringent action. The BET specific surface area is more preferably 12 $m^2/g$ or more, still more preferably 14 $m^2/g$ or more.

The zinc oxide particles of the present disclosure preferably have a ratio (BET specific surface area/median size) of 4 or more. In the zinc oxide particles of the present disclosure, it is easy to increase the BET specific surface area relative to the median size by its specific shape. The particles having the ratio (BET specific surface area/median size) within the above-mentioned range are preferred because the particles can maximally exhibit effects including an antibacterial property and an astringent action which are intrinsic to zinc oxide and the particles are zinc oxide particles having good handling property. The ratio (BET specific surface area/median size) is more preferably 5 or more, still more preferably 10 or more.

A method for producing the spherical zinc oxide particles of the present disclosure is not particularly limited but, for example, includes a method which comprises a step (1) of neutralizing a zinc salt aqueous solution by an alkali aqueous solution wherein said step (1) is performed in the presence of a hydrophilic dispersant. Such a method is one aspect of the present disclosure.

In the method for producing the spherical zinc oxide particles of the present disclosure, the hydrophilic dispersant is added when a crystal is deposited by a reaction of the zinc salt aqueous solution with the alkali. Thereby, besides the dispersion effect of the hydrophilic dispersant, an effect for maintaining the particle growth rate caused by the adsorption of the hydrophilic dispersant onto the reaction points on the obtained particle surface layer are utilized. The present inventors found that spherical zinc oxide particles consisting of integrated plate-like particles having a sharp particle size distribution which are conventionally unknown can be prepared by the above-mentioned method.

In this production method, the zinc salt aqueous solution is used as a raw material. A zinc salt which can be used as a raw material is not particularly limited but includes zinc salts of hydrochloric acid, nitric acid, sulfuric acid, acetic acid, oxalic acid, and fatty acids, and other organic acid zinc salts. The zinc salts may be used singly or two or more of them may be used in admixture.

As the zinc salt aqueous solution, for example, a solution prepared by dissolving the zinc salt in water in a concentration of 0.001 to 4.0 mol/l may be used. The zinc salt aqueous solution may contain other components such as water miscible organic solvents and so on, within a range where the object of the present disclosure is not disturbed.

The alkali component contained in the alkali aqueous solution is not particularly limited but includes sodium hydroxide, potassium hydroxide, lithium hydroxide, and so on. The concentration of the alkali aqueous solution is preferably 0.002 to 40.0 mol/l. The pH thereof is preferably 10.0 to 14.0.

The alkali aqueous solution may contain some components other than the alkali aqueous solution and the hydrophilic dispersant within a range where the object of the present disclosure is not disturbed.

In regards to the addition amount of the alkali aqueous solution, the content of an alkali component is preferably 2 to 10 relative to zinc ion 1 mol. It is preferred to adjust the content within the above-mentioned range because zinc oxide particles having the characteristic shape, being the spherical shape consisting of integrated plate-like particles, can be obtained. In regards to the addition amount of the alkali aqueous solution, the content of an alkali component is more preferably 2 to 8 mols relative to zinc ion 1 mol, still more preferably 3 to 6 mols.

In the step (1), the neutralizing method is not particularly limited but includes a method comprising stirring the alkali aqueous solution in a vessel and adding the zinc salt aqueous solution thereto, a method comprising stirring the zinc salt aqueous solution in a vessel and adding the alkali aqueous solution thereto, and a method comprising mixing the two solutions at a constant rate using a magnet pump and/or a roller pump.

The hydrophilic dispersant is not particularly limited but includes, for example, polycarboxylic acid and salts thereof, alkyl sulfonic acid and salts thereof, alkylbenzene sulfonic acid and salts thereof, naphthalene sulfonic acid and salts thereof, polyether alkyl sulfonic acid and salts thereof, alkylbetaines, polyethers and derivatives thereof, polyetheralkyl ethers, polyoxyalkylene alkenyl phenyl ethers, sorbitan fatty acid esters, polyether sorbitan fatty acid esters, polyether fatty acid esters, glyceryl fatty acid esters, polyether hydrogenated castor oil, polyether alkylamines, polyether-modified silicones, polyglyceryl-modified silicones, polyhydric alcohols, and alkyl-modified polyhydric alcohols. Any of anionic type, cationic type, and nonionic type compounds may be used, but nonionic type compounds are preferred because they are less likely to be hardly affected by the water hardness and an electrolyte, easy to handle, and can be used with other various surfactants. In addition, the HLB value is preferably 10.0 to 20 because the hydrophilic dispersant sufficiently dissolved in water to obtain the dispersion effect of the hydrophilic dispersant and the particle growth rate can be maintained by the adsorption of the hydrophilic dispersant onto the reaction points on the obtained particle surface layer. Two or more of the hydrophilic dispersant may be used in combination. In this specification, the HLB value is obtained according to the Griffin's equation;

$$\text{HLB} = (\text{total molecular weight of hydrophilic groups of the dispersant/molecular weight of the dispersant}) \times (100/5)$$

The adding method of the hydrophilic dispersant is not particularly limited on condition that the hydrophilic dispersant is present in the system during the progression of the reaction. For example, the hydrophilic dispersant may be mixed in the zinc salt aqueous solution followed by the progress of the reaction, and the hydrophilic dispersant may be mixed in the alkali aqueous solution. In addition, a method which comprises preparing a hydrophilic dispersant solution separately, and mixing and reacting three components at the same time, may be used.

The hydrophilic dispersant is preferably contained in the concentration of 0.1 to 20 weight % relative to the total aqueous solution.

The reaction temperature in the step (1) is not particularly limited but may be 10 to 110° C.

The obtained zinc oxide particles after the reaction may be subjected to conventional treatments such as a filtration, a water washing, a drying and so on. The zinc oxide particles thus obtained may be pulverized or classified by sieving as necessary. Examples of methods for classification by sieving may include wet classification and dry classification.

The production method of present disclosure has an advantage that zinc oxide particles are obtained directly without a thermal decomposition step such as calcinating. However, a calcinating may be performed for the improvement of crystallinity.

The zinc oxide particle of the present disclosure may be subjected to a surface treatment. The surface treatment is not particularly limited but includes surface treatments with a surface treatment agent selected from an organic silicon compound, an organic aluminum compound, an organic titanium compound, a higher fatty acid, a higher fatty acid ester, a metallic soap, a polyhydric alcohol and an alkanolamine. The treatment amount of the surface treatment agent can be appropriately set according to the particle diameter of the zinc oxide particle.

The spherical zinc oxide particle consisting of integrated plate-like particles of the present disclosure may be used as a component of a cosmetic. Such cosmetic is one aspect of the present disclosure. The spherical zinc oxide particle consisting of integrated plate-like particles can be used suitably in cosmetics because it gives a smooth feeling and has a superior performance in the ultraviolet blocking property. The cosmetics of the present disclosure may include a foundation, a makeup base, an eye shadow, a cheek rouge, a mascara, a lipstick, and a sunscreen agent. The cosmetic of the present disclosure can be in any form, for example, a form of an oil-based cosmetic, a water-based cosmetic, an O/W type cosmetic, or a W/O type cosmetic. Among them, the particles can be used especially suitably in makeup cosmetics such as a foundation, a makeup base, and an eye shadow.

For the cosmetic of the present disclosure, any aqueous component or oily component that can be used in the field of cosmetics can be used in combination in addition to the components composing the mixture. The aqueous component and oily component described above are not particularly limited, and examples thereof may include those containing components such as oils, surfactants, moisturizers, higher alcohols, sequestrants, natural and synthetic polymers, water-soluble and oil-soluble polymers, UV blocking agents, various extracts, inorganic and organic pigments, inorganic and organic clay minerals and other powders, inorganic and organic pigments treated with metallic soap or silicone, coloring materials such as organic dyes, preservatives, antioxidants, dyes, thickeners, pH adjusters, perfumes, cooling-sensation agents, antiperspirants, disinfectants, and skin activators. Specifically, a desired cosmetic can be produced in the usual manner using any one or more of the components listed below. The amounts of these components incorporated are not particularly restricted as long as they do not interfere with the effects of the present disclosure.

The oil is not particularly limited, and examples thereof may include avocado oil, camellia oil, turtle oil, macadamia nut oil, corn oil, mink oil, olive oil, rapeseed oil, egg-yolk oil, sesame oil, persic oil, wheat germ oil, sasanqua oil, castor oil, linseed oil, safflower oil, cottonseed oil, perilla oil, soybean oil, arachis oil, tea seed oil, kaya oil, rice bran oil, Japanese tung oil, jojoba oil, germ oil, triglycerol, glycerol trioctanoate, glycerol triisopalmitate, cacao butter, coconut oil, horse fat, palm oil, beef tallow, mutton tallow, hydrogenated beef tallow, palm kernel oil, lard, beef bone fat, hydrogenated oil, neatsfoot oil, Japan wax, hydrogenated castor oil, beeswax, candelilla wax, cotton wax, carnauba wax, bayberry wax, insect wax, spermaceti wax, montan wax, bran wax, lanolin, kapok wax, lanolin acetate, liquid lanolin, sugarcane wax, isopropyl lanolate, hexyl laurate, reduced lanolin, hard lanolin, shellac wax, POE lanolin alcohol ether, POE lanolin alcohol acetate, POE cholesterol ether, polyethylene glycol lanolate, POE hydrogenated lanolin alcohol ether, liquid paraffin, ozokerite, pristane, paraffin, ceresin, squalene, vaseline, and microcrystalline wax.

The lipophilic nonionic surfactant is not particularly limited, and examples thereof may include sorbitan fatty acid esters such as sorbitan monooleate, sorbitan monoisostearate, sorbitan monolaurate, sorbitan monopalmitate, sorbitan monostearate, sorbitan sesquioleate, sorbitan trioleate, diglycerol sorbitan penta-2-ethylhexylate, and diglycerol sorbitan tetra-2-ethylhexylate; (poly)glycerin fatty acid esters such as glycerol mono-cottonseed oil fatty acid, glycerol monoerucate, glycerol sesquioleate, glycerol monostearate, α,α'-glycerol oleate pyroglutamate, and glycerol monostearate malate; propylene glycol fatty acid esters such as propylene glycol monostearate; hydrogenated castor oil derivatives; and glycerol alkyl ethers.

The hydrophilic nonionic surfactant is not particularly limited, and examples thereof may include POE sorbitan fatty acid esters such as POE sorbitan monooleate, POE sorbitan monostearate and POE sorbitan tetraoleate; POE sorbitol fatty acid esters such as POE sorbitol monolaurate, POE sorbitol monooleate, POE sorbitol pentaoleate and POE sorbitol monostearate; POE glycerin fatty acid esters such as POE glycerin monostearate, POE glycerin monoisostearate and POE glycerin triisostearate; POE fatty acid esters such as POE monooleate, POE distearate, POE monodioleate and ethylene glycol distearate; POE alkyl ethers such as POE lauryl ether, POE oleyl ether, POE stearyl ether, POE behenyl ether, POE 2-octyldodecyl ether and POE cholestanol ether; POE alkyl phenyl ethers such as POE octyl phenyl ether, POE nonyl phenyl ether and POE dinonyl phenyl ether; Pluaronic types such as Pluronic; POE/POP alkyl ethers such as POE/POP cetyl ether, POE/POP 2-decyltetradecyl ether, POE/POP monobutyl ether, POE/POP hydrogenated lanolin and POE/POP glycerin ether; tetra-POE/tetra-POP ethylenediamine condensation products such as Tetronic; POE castor oil hydrogenated castor oil derivatives such as POE castor oil, POE hydrogenated castor oil, POE hydrogenated castor oil monoisostearate, POE hydrogenated castor oil triisostearate, POE hydrogenated castor oil monopyroglutamic acid monoisostearic acid diester and POE hydrogenated castor oil maleic acid; POE beeswax/lanolin derivatives such as POE sorbitol beeswax; alkanolamides such as coconut oil fatty acid diethanolamide, lauric acid monoethanolamide and fatty acid isopropanol amide; POE propylene glycol fatty acid esters; POE alkylamines; POE fatty acid amides; sucrose fatty acid esters; POE nonylphenyl formaldehyde condensation products; alkyl ethoxy dimethylamine oxides; and trioleyl phosphoric acid.

Examples of other surfactants include anionic surfactants such as fatty acid soaps, higher-alkyl sulfuric ester salts, POE triethanolamine lauryl sulfate, and alkyl ether sulfuric ester salts; cationic surfactants such as alkyl trimethylammonium salts, alkyl pyridinium salts, alkyl quaternary ammonium salts, alkyl dimethylbenzyl ammonium salts, POE alkylamines, alkylamine salts, and polyamine fatty acid derivatives; and amphoteric surfactants such as imidazoline amphoteric surfactants and betaine surfactants. They may be incorporated within the bounds of not causing any problems with stability and skin irritation.

The moisturizer is not particularly limited, and examples thereof may include xylitol, sorbitol, maltitol, chondroitin sulfate, hyaluronic acid, mucoitinsulfuric acid, caronic acid, atelocollagen, cholesteryl-12-hydroxystearate, sodium lactate, bile salts, dl-pyrrolidone carboxylate, short-chain soluble collagens, diglycerol (EO) PO adducts, *Rosa roxburghii* extract, yarrow extract, and melilot extract.

The higher alcohol is not particularly limited, and examples thereof may include linear alcohols such as lauryl alcohol, cetyl alcohol, stearyl alcohol, behenyl alcohol, myristyl alcohol, oleyl alcohol, and cetostearyl alcohol; and branched alcohols such as monostearyl glycerol ether (batyl alcohol), 2-decyltetradecynol, lanolin alcohol, cholesterol, phytosterol, hexyldodecanol, isostearyl alcohol, and octyldodecanol.

The sequestrant is not particularly limited, and examples thereof may include 1-hydroxyethane-1,1-diphosphonic acid, 1-hydroxyethane-1,1-diphosphonic acid tetrasodium salt, sodium citrate, sodium polyphosphate, sodium metaphosphate, gluconic acid, phosphoric acid, citric acid, ascorbic acid, succinic acid, and edetic acid.

The natural water-soluble polymer is not particularly limited, and examples thereof may include plant-derived polymers such as gum arabic, tragacanth gum, galactan, guar gum, carob gum, karaya gum, carrageenan, pectin, agar, quince seed (quince), algal colloid (algal extract), starch (rice, corn, potato, wheat), and glycyrrhizinic acid; microorganism-derived polymers such as xanthan gum, dextran, succinoglucan, and pullulan; and animal-derived polymers such as collagen, casein, albumin, and gelatin.

The semisynthetic water-soluble polymer is not particularly limited, and examples thereof may include starch polymers such as carboxymethyl starch and methyl hydroxypropyl starch; cellulose polymers such as methyl cellulose, nitro cellulose, ethyl cellulose, methyl hydroxypropyl cellulose, hydroxyethyl cellulose, cellulose sodium sulfate, hydroxypropyl cellulose, sodium carboxymethylcellulose (CMC), crystalline cellulose, and cellulose powder; and alginate polymers such as sodium alginate and propylene glycol alginate.

The synthetic water-soluble polymer is not particularly limited, and examples thereof may include vinyl polymers such as polyvinyl alcohol, polyvinyl methyl ether, and polyvinyl pyrrolidone; polyoxyethylene polymers such as polyethylene glycol 20,000, polyethylene glycol 40,000, and polyethylene glycol 60,000; copolymers such as polyoxyethylene-polyoxypropylene copolymers; acrylic polymers such as sodium polyacrylate, polyethylacrylate, and polyacrylamide; polyethyleneimine; and cationic polymers.

The inorganic water-soluble polymer is not particularly limited, and examples thereof may include bentonite, magnesium aluminum silicate (Veegum), laponite, hectorite, and silicic anhydride.

The ultraviolet blocking agent is not particularly limited, and examples thereof may include benzoic acid-based ultraviolet blocking agents such as paraaminobenzoic acid (hereinafter, abbreviated as PABA), PABA monoglycerin ester, N,N-dipropoxy PABA ethyl ester, N,N-diethoxy PABA ethyl ester, N,N-dimethyl PABA ethyl ester and N,N-dimethyl PABA butyl ester; anthranilic acid-based ultraviolet blocking agents such as homomenthyl-N-acetyl anthranilate; salicylic acid-based ultraviolet blocking agents such as amyl salicylate, menthyl salicylate, homomenthyl salicylate, octyl salicylate, phenyl salicylate, benzyl salicylate and p-isopropanol phenyl salicylate; cinnamic acid-based ultraviolet blocking agents such as octyl cinnamate, ethyl-4-isopropyl cinnamate, methyl-2,5-diisopropyl cinnamate, ethyl-2,4-diisopropyl cinnamate, methyl-2,4-diisopropyl cinnamate, propyl-p-methoxy cinnamate, isopropyl-p-methoxy cinnamate, isoamyl-p-methoxy cinnamate, 2-ethoxyethyl-p-methoxy cinnamate, cyclohexyl-p-methoxy cinnamate, ethyl-α-cyano-β-phenyl cinnamate, 2-ethylhexyl-α-cyano-β-phenyl cinnamate and glycerylmono-2-ethylhexanoyl-diparamethoxy cinnamate; benzophenone-based ultraviolet blocking agents such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone and 4-hydroxy-3-carboxybenzophenone; 3-(4'-methylbenzylidene)-d,l-camphor, 3-benzylidene-d,l-camphor, urocanic acid, urocanic acid ethyl ester, 2-phenyl-5-methylbenzoxazole, 2,2'-hydroxy-5-methylphenyl benzotriazole, 2-(2'-hydroxy-5'-t-octylphenyl)benzotriazole, 2-(2'-hydroxy-5'-methylphenyl)benzotriazole, dibenzalazine, dianisoylmethane, 4-methoxy-4'-t-butyldibenzoylmethane and 5-(3,3-dimethyl-2-norbornylidene)-3-pentane-2-one.

Other chemical components are not particularly limited, and examples thereof may include vitamins such as vitamin A oil, retinol, retinol palmitate, inositol, pyridoxine hydrochloride, benzyl nicotinate, nicotinamide, DL-α-tocopherol nicotinate, magnesium ascorbyl phosphate, 2-O-α-D-glucopyranosyl-L-ascorbic acid, vitamin D2 (ergocalciferol), DL-α-tocopherol, DL-α-tocopherol acetate, pantothenic acid, and biotin; hormones such as estradiol and ethynyl estradiol; amino acids such as arginine, aspartic acid, cystine, cysteine, methionine, serine, leucine, and tryptophan; anti-inflammatory agents such as allantoin and azulene; whitening agents such as arbutin; astringents such as tannic acid; refrigerants such as L-menthol and camphor, sulfur, lysozyme chloride, and pyridoxine chloride.

Various kinds of extracts are not particularly limited, and examples thereof may include *Houttuynia cordata* extract, Phellodendron bark extract, melilot extract, dead nettle extract, licorice extract, peony root extract, soapwort extract, luffa extract, cinchona extract, strawberry geranium extract, *sophora* root extract, nuphar extract, fennel extract, primrose extract, rose extract, rehmannia root extract, lemon extract, lithospermum root extract, aloe extract, calamus root extract, *eucalyptus* extract, field horsetail extract, sage extract, thyme extract, tea extract, seaweed extract, cucumber extract, clove extract, bramble extract, lemon balm extract, carrot extract, horse chestnut extract, peach extract, peach leaf extract, mulberry extract, knapweed extract, *hamamelis* extract, placenta extract, thymic extract, silk extract, and licorice extract.

Examples of the various kinds of powders may include bright coloring pigments such as red oxide, yellow iron oxide, black iron oxide, mica titanium, iron oxide-coated mica titanium and titanium oxide-coated glass flakes, inorganic powders such as those of mica, talc, kaolin, sericite, titanium dioxide and silica, and organic powders such as polyethylene powder, nylon powder, crosslinked polystyrene, cellulose powder and silicone powder. Preferably, part or all of the powder component may be subjected to a hydrophobization treatment by well-known method with a substance such as a silicone, a fluorine compound, a metallic soap, an oily agent or an acyl glutamic acid salt for improvement of sensory characteristics and improvement of makeup retainability. Other zinc oxide particles that do not fall under the present disclosure may be mixed and used.

The spherical zinc oxide particle consisting of integrated plate-like particles of the present disclosure can also be used as a thermal conductive filler.

When the spherical zinc oxide particle consisting of integrated plate-like particles of the present disclosure is used as a thermal conductive filler, it may be used either alone or in combination with other thermal conductive fillers. It is preferable to use the thermal conductive filler of the present disclosure at a ratio of 10 to 90% by volume based on the total amount of a thermal conductive composition such as a resin composition or a grease composition regardless of whether it is used alone or used in combination with other thermal conductive fillers.

The spherical zinc oxide particle consisting of integrated plate-like particles of the present disclosure can also be used in combination with a thermal conductive filler having a different particle diameter when used as a thermal conductive filler. The thermal conductive filler that can be used in combination is not particularly limited, and examples thereof may include metal oxides such as magnesium oxide, titanium oxide and aluminum oxide, aluminum nitride, boron nitride, silicon carbide, silicon nitride, titanium nitride, metal silicon and diamond. Further, zinc oxide other than the round-shaped zinc oxide particle described above can be used in combination. The thermal conductive filler used in combination may have any shape such as a spherical shape, a needle shape, a rod shape or a plate shape.

When the spherical zinc oxide particle consisting of integrated plate-like particles is used as a thermal conductive filler, it can be mixed with a resin and used as a thermal conductive resin composition. In this case, the resin to be used may be either a thermoplastic resin or a thermosetting resin, and examples thereof may include resins such as an epoxy resin, a phenol resin, a polyphenylene sulfide (PPS) resin, a polyester-based resin, polyamide, polyimide, polystyrene, polyethylene, polypropylene, polyvinyl chloride, polyvinylidene chloride, a fluororesin, polymethyl methacrylate, an ethylene/ethyl acrylate copolymer (EEA) resin, polycarbonate, polyurethane, polyacetal, polyphenylene ether, polyether imide, an acrylonitrile-butadiene-styrene copolymer (ABS) resin, a liquid crystal resin (LCP), a silicone resin and an acrylic resin.

The thermal conductive resin composition of the present disclosure may be a (1) resin composition for thermoforming, which is obtained by kneading a thermoplastic resin and the spherical zinc oxide particle consisting of integrated plate-like particles in a molten state, or (2) a resin composition obtained by kneading a thermosetting resin and the spherical zinc oxide particle consisting of integrated plate-like particles, followed by heating the mixture to be cured, or (3) a resin composition for coatings, which is obtained by dispersing the spherical zinc oxide particle consisting of integrated plate-like particles in a resin solution or dispersion.

When the thermal conductive resin composition of the present disclosure is a resin composition for thermoforming, a resin component can be freely selected according to a use purpose. For example, when the resin composition is bonded and adhered to a heat source and a radiator plate, a resin having high adhesiveness and a low hardness, such as a silicone resin or an acrylic resin, may be selected.

When the thermal conductive resin composition is a resin composition for coatings, the resin does not necessarily have to have curability. The coating may be a solvent-based coating containing an organic solvent, or a water-based coating with a resin dissolved or dispersed in water.

When the spherical zinc oxide particle consisting of integrated plate-like particles of the present disclosure is used as a thermal conductive filler, it can be mixed with abase oil containing a mineral oil or a synthetic oil, and used as a thermal conductive grease. When the spherical zinc oxide particle consisting of integrated plate-like particles is used as the thermal conductive grease, an α-olefin, a diester, a polyol ester, a trimellitic acid ester, a polyphenyl ether, an alkyl phenyl ether or the like can be used as a synthetic oil. The spherical zinc oxide particle consisting of integrated plate-like particles can also be mixed with a silicone oil and used as a thermal conductive grease.

When the spherical zinc oxide particle consisting of integrated plate-like particles of the present disclosure is used as a thermal conductive filler, other components can be used in combination. Examples of other components that can be used in combination may include thermal conductive fillers other than zinc oxide, such as metal oxides such as magnesium oxide, titanium oxide and aluminum oxide, aluminum nitride, boron nitride, silicon carbide, silicon nitride, titanium nitride, metal silicon, and diamond; resins; and surfactants.

When the spherical zinc oxide particle consisting of integrated plate-like particles of the present disclosure is used in combination with a zinc oxide particle having a smaller particle diameter or another thermal conductive filler, a superior thermal conductive performance can be achieved. The zinc oxide particle having a smaller particle diameter and another thermal conductive filler that are used in combination, may have any shape such as a spherical shape, a needle shape, a rod shape or a plate shape.

The spherical zinc oxide particle consisting of integrated plate-like particles of the present disclosure can be used in the fields of vulcanization accelerators for rubber, pigments for coatings/inks, electronic components such as ferrites and varistors, pharmaceuticals and so on in addition to the cosmetics and thermal conductive fillers described above.

EXAMPLES

Hereinafter, the present disclosure will be explained with reference to examples. However, the present disclosure is not limited to these examples.

Example 1

Figure 2:
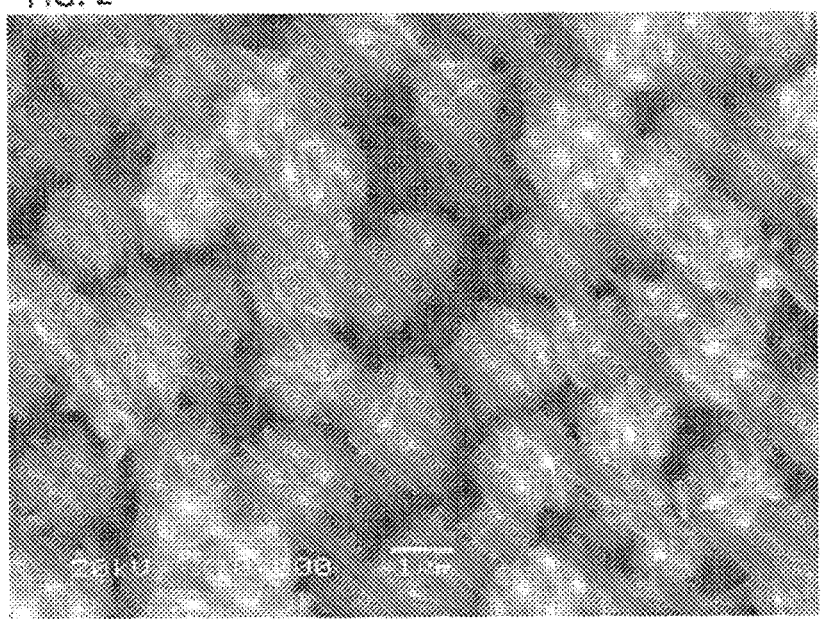
FIG. 2 is a scanning electron microscope photograph of zinc oxide particles obtained in Example 1. The magnification of this photograph is higher than that of FIG. 1.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Sodium hydroxide (manufactured by Kishida Chemical, purity: 98%) 31.3 g was dissolved in water to prepare 758 ml of sodium hydroxide aqueous solution such that the concentration of sodium hydroxide is 1.0 mol/l, and 2.125 g of TW-O 120 V (manufactured by KaO, polyoxyethylene sorbitan monooleate, HLB14.9) was added thereto and sufficiently mixed. Next, the sodium hydroxide aqueous solution was stirred at a rotation speed of 300 rpm using a stirring machine, and the zinc acetate aqueous solution was added for 10 seconds while stirring and then the mixture was stirred for 30 minutes to advance the reaction. After the completion of reaction, the mixture was filtered, washed with water, and dried to obtain Spherical zinc oxide particles consisting of integrated plate-like particles having a median size of 1.11 μm. The size and form of the obtained particles were observed with a scanning electron microscope JSM-5600 (manufactured by JEOL Ltd.). The obtained electron microscope photograph is shown in FIG. 1. Further, an electron microscope photograph photographed at higher magnification was shown in FIG. 2. The obtained particles were analyzed by X-ray diffractometer UltimaIII (manufactured by Rigaku Corporation). The obtained X-ray diffraction spectrum was shown in FIG. 3. The results of evaluating the physical properties of the obtained particles and the physical properties of the coating film were shown in Table 1.

Example 2

Figure 4:
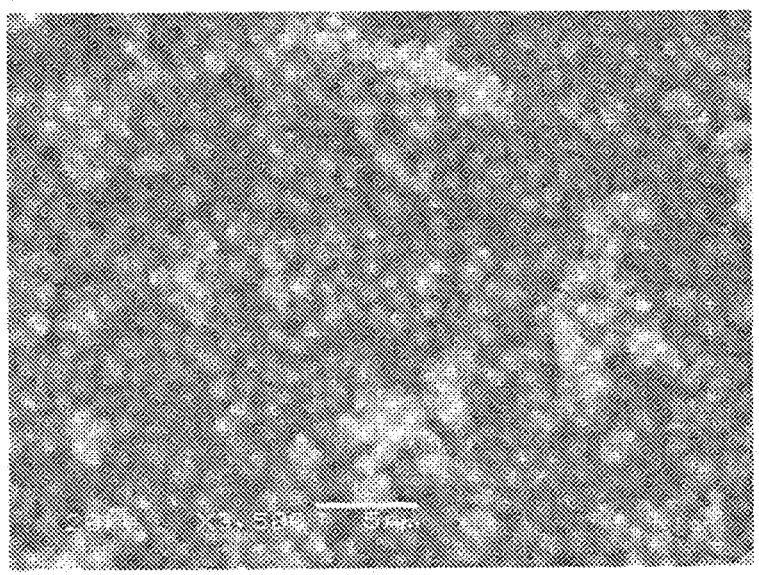
FIG. 4 is a scanning electron microscope photograph of zinc oxide particles obtained in Example 2.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Potassium hydroxide (manufactured by Kishida Chemical, purity: 85%) 50.0 g was dissolved in water to prepare 758 ml of potassium hydroxide aqueous solution such that the concentration of potassium hydroxide is 1.0 mol/l, and 2.125 g of TW-O 120 V (manufactured by KaO, polyoxyethylene sorbitan monooleate, HLB14.9) was added thereto and sufficiently mixed. Next, the potassium hydroxide aqueous solution was stirred at a rotation speed of 300 rpm using a stirring machine, and the zinc acetate aqueous solution was added for 10 seconds while stirring and then the mixture was stirred for 30 minutes to advance the reaction. After the completion of reaction, the mixture was filtered, washed with water, and dried to obtain spherical zinc oxide particles consisting of integrated plate-like particles having a median size of 1.05 μm. The size and form of the obtained particles were observed with a scanning electron microscope JSM-5600 (manufactured by JEOL Ltd.). The obtained electron microscope photograph is shown in FIG. 4. The results of evaluating the physical properties of the obtained particles and the physical properties of the coating film were shown in Table 1.

Example 3

Figure 5:
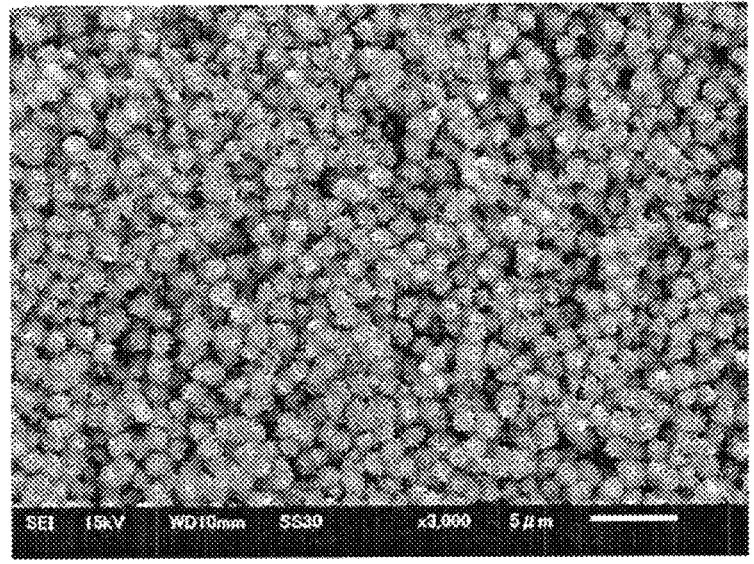
FIG. 5 is a scanning electron microscope photograph of zinc oxide particles obtained in Example 3.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Sodium hydroxide (manufactured by Kishida Chemical, purity: 98%) 31.3 g was dissolved in water to prepare 758 ml of sodium hydroxide aqueous solution such that the concentration of sodium hydroxide is 1.0 mol/l, and 2.125 g of TW-O 120 V (manufactured by KaO, polyoxyethylene sorbitan monooleate, HLB14.9) was added thereto and sufficiently mixed. Next, the sodium hydroxide aqueous solution was stirred at a rotation speed of 300 rpm using a stirring machine, and the zinc acetate aqueous solution was added for 300 seconds using a roller pump while stirring and then the mixture was stirred for 30 minutes to advance the reaction. After the completion of reaction, the mixture was filtered, washed with water, and dried to obtain spherical zinc oxide particles consisting of integrated plate-like particles having a median size of 1.00 μm. The size and form of the obtained particles were observed with a scanning electron microscope JSM-6510A (manufactured by JEOL Ltd.). The obtained electron microscope photograph is shown in FIG. 5. The results of evaluating the physical properties of the obtained particles and the physical properties of the coating film were shown in Table 1.

Example 4

Figure 6:
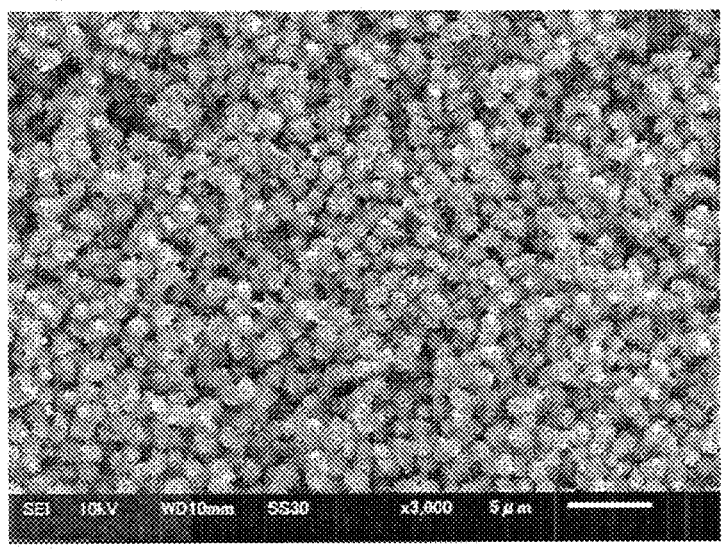
FIG. 6 is a scanning electron microscope photograph of zinc oxide particles obtained in Example 4.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Sodium hydroxide (manufactured by Kishida Chemical, purity: 98%) 23.8 g was dissolved in water to prepare 758 ml of sodium hydroxide aqueous solution such that the concentration of sodium hydroxide is 0.8 mol/l, and 2.125 g of TW-O 120 V (manufactured by KaO, polyoxyethylene sorbitan monooleate, HLB14.9) was added thereto and sufficiently mixed. Next, the sodium hydroxide aqueous solution was stirred at a rotation speed of 300 rpm using a stirring machine, and the zinc acetate aqueous solution was added for 600 seconds using a roller pump while stirring and then the mixture was stirred for 30 minutes to advance the reaction. After the completion of reaction, the mixture was filtered, washed with water, and dried to obtain spherical zinc oxide particles consisting of integrated plate-like particles having a median size of 1.02 μm. The size and form of the obtained particles were observed with a scanning electron microscope JSM-6510A (manufactured by JEOL Ltd.). The obtained electron microscope photograph is shown in FIG. 6. The results of evaluating the physical properties of the obtained particles and the physical properties of the coating film were shown in Table 1.

Example 5

Figure 7:
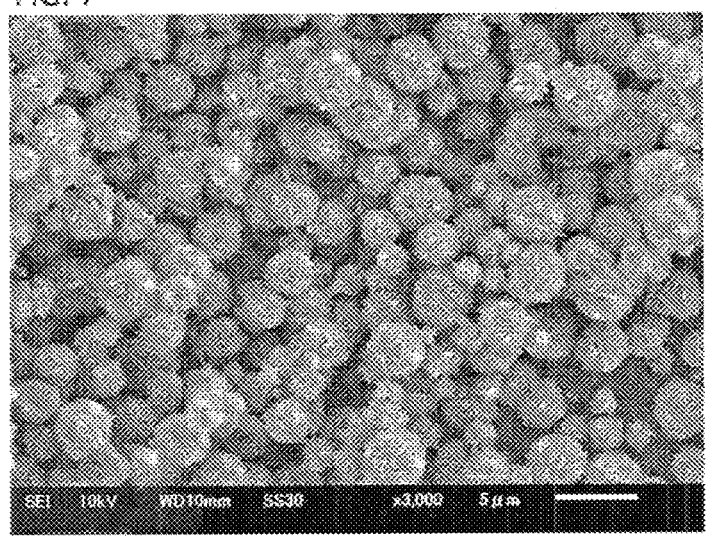
FIG. 7 is a scanning electron microscope photograph of zinc oxide particles obtained in Example 5.
Figure 8:
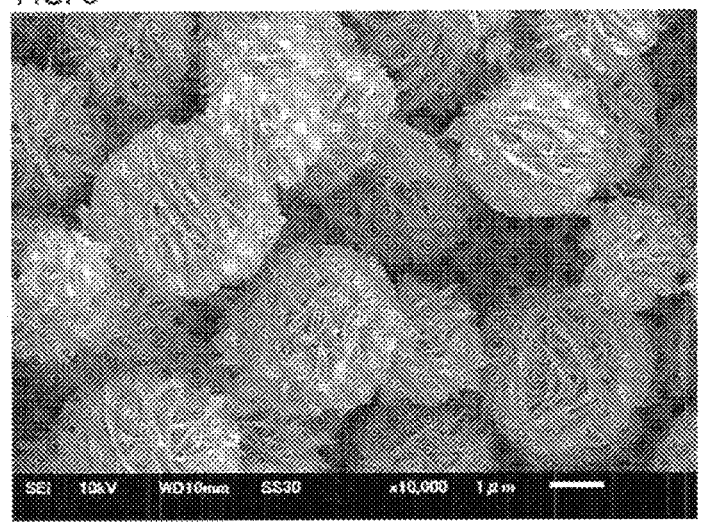
FIG. 8 is a scanning electron microscope photograph of zinc oxide particles obtained in Example 5. The magnification of this photograph is higher than that of FIG. 7.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Sodium hydroxide (manufactured by Kishida Chemical, purity: 98%) 31.3 g was dissolved in water to prepare 758 ml of sodium hydroxide aqueous solution such that the concentration of sodium hydroxide is 1.0 mol/l, and 2.125 g of TW-O 120 V (manufactured by KaO, polyoxyethylene sorbitan monooleate, HLB14.9) was added thereto and sufficiently mixed. Next, the sodium hydroxide aqueous solution and the zinc acetate aqueous solution were mixed by sending for 120 seconds with the use of a roller pump, respectively, to the inside of a magnet pump that is rotating at a rotation speed of 2700 rpm. After the mixing, the reaction solution was stirred for 5 minutes at 2700 rpm to advance the reaction. After the completion of reaction, the mixture was filtered, washed with water, and dried to obtain spherical zinc oxide particles consisting of integrated plate-like particles having a median size of 2.72 μm. The size and form of the obtained particles were observed with a scanning electron microscope JSM-6510A (manufactured by JEOL Ltd.). The obtained electron microscope photograph is shown in FIG. 7. Further, an electron microscope photograph photographed at higher magnification was shown in FIG. 8. The results of evaluating the physical properties of the obtained particles and the physical properties of the coating film were shown in Table 1.

Comparative Example 1

Figure 9:
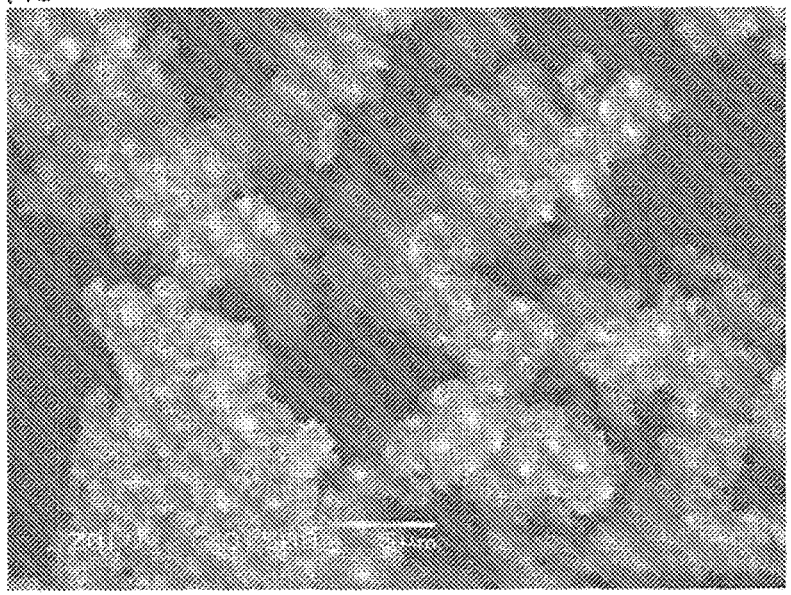
FIG. 9 is a scanning electron microscope photograph of zinc oxide particles obtained in Comparative Example 1.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Sodium hydroxide (manufactured by Kishida Chemical, purity: 98%) 31.3 g was dissolved in water to prepare 758 ml of sodium hydroxide aqueous solution such that the concentration of sodium hydroxide is 1.0 mol/l. Next, the sodium hydroxide aqueous solution was stirred at a rotation speed of 300 rpm using a stirring machine, and the zinc acetate aqueous solution was added thereto for 10 seconds while stirring and then the mixture was stirred for 30 minutes to advance the reaction. After the completion of reaction, the mixture was filtered, washed with water, and dried to obtain indefinite-shaped zinc oxide particles consisting of integrated plate-like particles having a median size of 4.12 μm. The size and form of the obtained particles were observed with a scanning electron microscope JSM-5600 (manufactured by JEOL Ltd.). The obtained electron microscope photograph is shown in FIG. 9. The results of evaluating the physical properties of the obtained particles and the physical properties of the coating film were shown in Table 1.

Comparative Example 2

Figure 10:
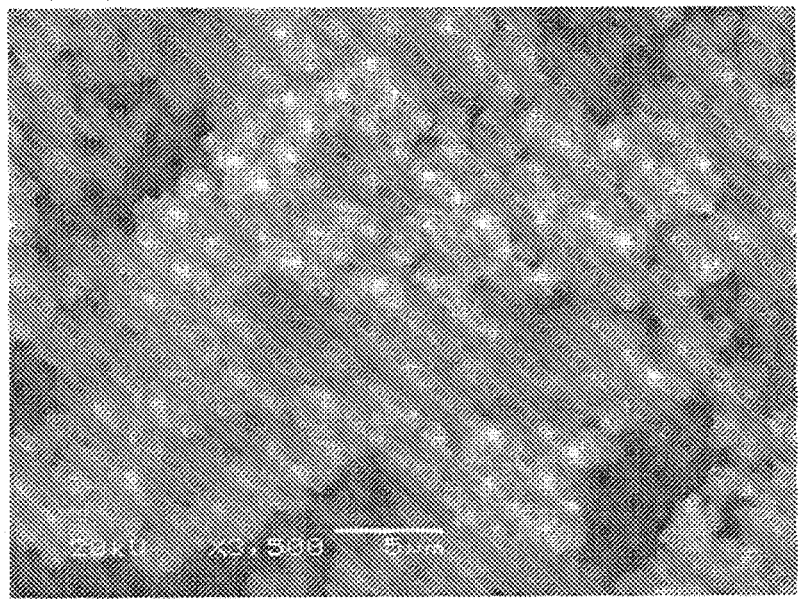
FIG. 10 is a scanning electron microscope photograph of zinc oxide particles obtained in Comparative Example 2.

Zinc acetate dihydrate (manufactured by Kishida Chemical, purity: 98%) 32 g was dissolved in water to prepare 116 ml of zinc acetate aqueous solution having zinc acetate dihydrate concentration of 1.26 mol/l. Potassium hydroxide (manufactured by Kishida Chemical, purity: 85%) 50.0 g was dissolved in water to prepare 758 ml of potassium hydroxide aqueous solution such that the concentration of potassium hydroxide is 1.0 mol/l. Next, the potassium hydroxide aqueous solution was stirred at a rotation speed of 300 rpm using a stirring machine, and the zinc acetate aqueous solution was added thereto for 10 seconds while stirring and then the mixture was stirred for 30 minutes to advance the reaction. After the completion of reaction, the mixture was filtered, washed with water, and dried to obtain indefinite-shaped zinc oxide particles consisting of integrated plate-like particles having a median size of 3.05 μm. The size and form of the obtained particles were observed with a scanning electron microscope JSM-5600 (manufactured by JEOL Ltd.). The obtained electron microscope photograph is shown in FIG. 10. The results of evaluating the physical properties of the obtained particles and the physical properties of the coating film were shown in Table 1.

Comparative Example 3

Figure 11:
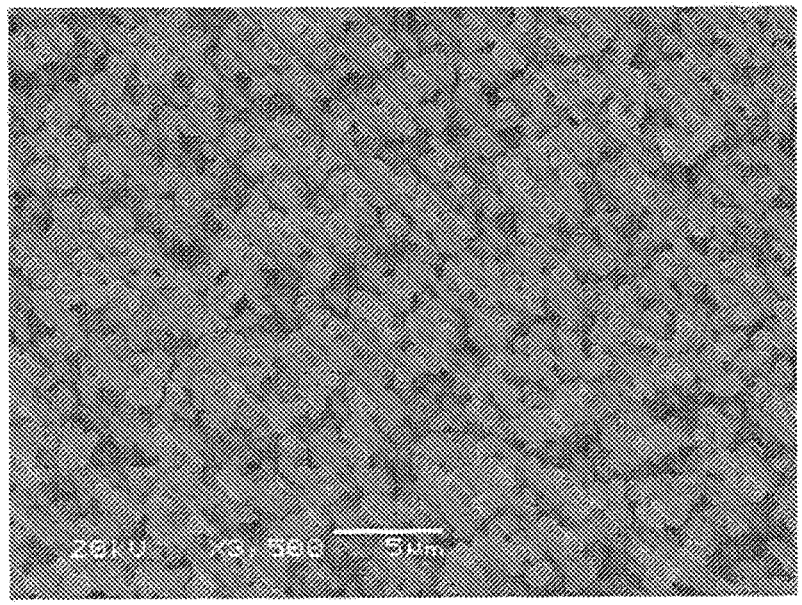
FIG. 11 is a scanning electron microscope photograph of LPZINC-2 being commercially available zinc oxide particles used in Comparative Example 3.

LPZINC-2 (manufactured by Sakai Chemical Industry Co., Ltd., median size: 1.63 μm) was evaluated in the same manner as in the examples. The electron microscope photograph is shown in FIG. 11. The results of evaluating the physical properties of the obtained particles and the physical properties of the coating film are shown in Table 1.

plane; the (002) plane of the zinc oxide particle of Example 1 is detected greatly and the value of I(002)/I(100) becomes bigger.

(Median Size, D10, D90, and D90/D10)

Herein, D50, D90 and D10 of particles are values measured by a laser diffraction/scattering particle size distribution measuring device LA-750 (manufactured by HORIBA, Ltd.). The zinc oxide particle 0.5 g in each of examples and

TABLE 1

|  |  | Example 1 | Example 2 | Example 3 | Example 4 | Example 5 | Compar. Ex 1 | Compar. Ex. 2 | Compar. Ex. 3 |
|---|---|---|---|---|---|---|---|---|---|
| Preparation conditions | Zn source aqueous solution | Zinc acetate aqueous solution | | | | | | | |
|  | Amount of Zn source (g) | 32 | 32 | 32 | 32 | 32 | 32 | 32 | |
|  | Concentration of Zn source aqueous solution (mol/l) | 1.26 | 1.26 | 1.26 | 1.26 | 1.26 | 1.26 | 1.26 | |
|  | Amount of Zn source aqueous solution | 116 | 116 | 116 | 116 | 116 | 116 | 116 | |
|  | Neutralizer (Alkali component) | Sodium Hydroxide | Potassium hydroxide | Sodium hydroxide | Sodium hydroxide | Sodium hydroxide | Sodium hydroxide | Potassium hydroxide | |
|  | Amount of neutralizer (Alkali component) (g) | 31.3 | 50.0 | 31.3 | 23.8 | 31.3 | 31.3 | 50.0 | |
|  | Concentration of neutralizer aqueous solution (mol/l) | 1.0 | 1.0 | 1.0 | 0.8 | 1.0 | 1.0 | 1.0 | |
|  | Amount of neutralizer aqueous solution (ml) | 758 | 758 | 758 | 758 | 758 | 758 | 758 | |
|  | Amount of neutralizer (mol of alkali component) relative to amount of Zn source (mol of Zn) | 5 times | 5 times | 5 times | 4 times | 5 times | 5 times | 5 times | |
|  | Hydrophilic dispersant | Polyexyethylene sorbitan monooleate | | | | | | | |
|  | Amount of hydrophilic dispersant (g) | 2.125 | 2.125 | 2.125 | 2.125 | 2.125 | | | |
|  | Mixing time (sec.) | 10 | 10 | 300 | 600 | 120 | 10 | 10 | |
|  | Stirring rate (rpm) | 300 | 300 | 300 | 300 | 2700 | 300 | 300 | |
|  | Neutralizing reaction temperature (° C.) | 25 | 25 | 30 | 30 | 30 | 25 | 25 | |
|  | Neutralizing reaction time (min.) | 30 | 30 | 30 | 30 | 5 | 30 | 30 | |
| Physical properties of particles | Composition of obtained particle | Zinc oxide | Zinc oxide | Zinc oxide | Zinc oxide | Zinc oxide | Zinc oxide | Zinc oxide | Zinc oxide |
|  | Shape of obtained particle | Sphere consisting of integrated plate-like particles | | | | | Indefinite shape condisting of integrated plate-like particles | | Indefinite shape |
|  | Median size (μm) | 1.11 | 1.05 | 1.00 | 1.02 | 2.72 | 4.12 | 3.05 | 1.63 |
|  | D90 (μm) | 1.88 | 1.66 | 1.53 | 1.59 | 5.14 | 8.94 | 6.71 | 3.29 |
|  | D10 (μm) | 0.45 | 0.33 | 0.34 | 0.33 | 1.76 | 1.18 | 0.86 | 0.33 |
|  | D90/D10 | 4.2 | 4.4 | 4.5 | 4.8 | 2.9 | 7.6 | 7.8 | 10.1 |
|  | I(002)/I(100) | 1.2 | 1.0 | 1.0 | 1.1 | 1.2 | 1.0 | 0.9 | 0.7 |
|  | MIU (average friction coefficient) | 0.64 | 0.66 | 0.63 | 0.60 | 0.54 | 1.02 | 1.07 | 1.10 |
|  | MMD (mean deviation of friction coefficient) | 0.0095 | 0.0099 | 0.0095 | 0.0092 | 0.0088 | 0.0178 | 0.0194 | 0.0391 |
|  | BET specific surface area ($m^2/g$) | 15.6 | 15.9 | 15.4 | 15.5 | 30.8 | 7.9 | 9.1 | 1.0 |
|  | Ratio of BET specific surface area/median size | 14.0 | 15.1 | 14.5 | 15.2 | 11.3 | 1.9 | 3.0 | 0.6 |
| Physical properties of coating films | Total light transmittance 1 (%) | 17 | 22 | 18 | 21 | 24 | 20 | 23 | 57 |
|  | Total light transmittance 2 (%) | 17 | 22 | 19 | 22 | 25 | 21 | 24 | 63 |
|  | Parallel light transmittance 1 (%) | 56 | 64 | 58 | 62 | 66 | 66 | 85 | 42 |
|  | Parallel light transmittance 2 (%) | 77 | 79 | 78 | 78 | 78 | 81 | 80 | 53 |
|  | Diffusing light transmittance (%) | 58 | 56 | 55 | 60 | 48 | 25 | 22 | 20 |
|  | Total light transmittance 3 (%) | 82 | 82 | 80 | 79 | 85 | 84 | 87 | 83 |
|  | Haze (%) | 70 | 69 | 69 | 76 | 56 | 30 | 26 | 24 |

(Evaluation Method)

(X-Ray Diffraction Spectra, Composition of Obtained Particles)

Figure 3:
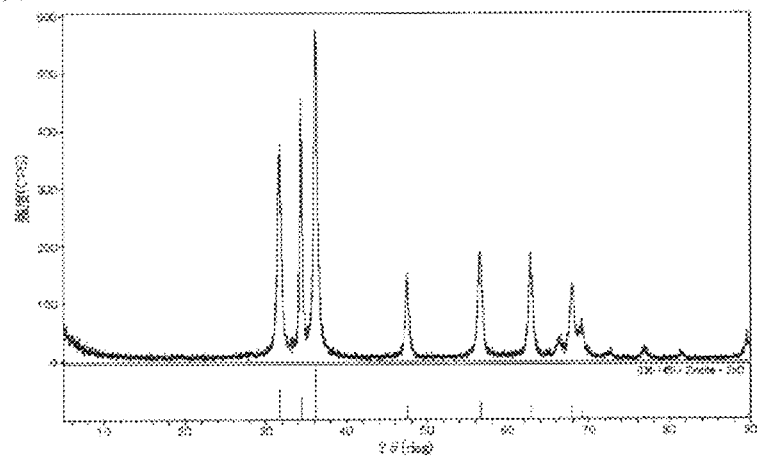
FIG. 3 is an X-ray diffraction spectrum of zinc oxide particles obtained in Example 1.

The X-ray diffraction spectra shown in FIG. 3 and the compositions of the obtained particles in Table 1 show results of performing analysis using an X-ray diffractometer UltimaIII (manufactured by Rigaku Corporation) having an X-Ray tube with copper. From these results, it is evident that zinc oxide is obtained in each examples. From FIG. 3, it is evident that the crystal growth of the obtained zinc oxide particle progresses in the direction of plate-like plane because I (002) that is a peak strength on the plate-like comparative examples was dissolved in 50 ml of an aqueous sodium hexametaphosphate solution in a concentration of 0.025% by weight in terms of sodium hexametaphosphate to thereby prepare a slurry, and a measurement was performed using the slurry. Before the measurements, the slurry was ultrasonic dispersed for 2 minutes with the use of an ultrasonic homogenizer US-600T (manufactured by NISSEI Corporation). Then, the measurement was performed under the condition that the cycling rate is 15, the ultrasonic dispersion time is 3 minutes, and the ultrasonic strength is 7. The measurement was performed with the relative refractive index of zinc oxide in examples and comparative examples set at 1.5. In this specification, median size denotes a 50% cumulative particle diameter on the volume basis, D90 denotes a 90% cumulative particle diameter on the volume basis, and D10 denotes a 10% cumulative particle diameter on the volume basis. A ratio of D90/D10 is calculated as an indicator of sharpness of the particle size distribution. The particle size distribution broadens as the value becomes larger, while the particle size distribution sharpens as the value becomes smaller.

(MIU (Average Friction Coefficient))

MIU (average friction coefficient) in Table 1 is determined by measuring the zinc oxide particles obtained in examples and comparative Examples with the use of KES-SE friction tester (manufactured by Kato Tech Co., Ltd.). A 25-mm-wide double-stick tape was stuck on a slide glass, and a powder was placed thereon and spread by a makeup puff. Next, MIU (average friction coefficient) of the obtained sample was measured with the use of KES-SE friction tester (manufactured by Kato Tech Co., Ltd.). The measurement was performed at a friction measurement load of 25 gf, at a surface measurement sample moving speed of 1 mm/sec, and a measurement distance range of 20 mm. As a sensor, a silicone contact piece (a friction piece of silicone rubber with irregular shape assumed as a human finger) was used. As the value of MIU (average friction coefficient) becomes smaller, the slippage of the obtained particles is good and the particle is slippery.

(MMD (Mean Deviation of Friction Coefficient))

MMD (mean deviation of friction coefficient) in Table 1 is determined by measuring the zinc oxide particles obtained in examples and comparative Examples with the use of KES-SE friction tester (manufactured by Kato Tech Co., Ltd.). A 25-mm-wide double-stick tape was stuck on a slide glass, and a powder was placed thereon and spread by a makeup puff. Next, MMD (mean deviation of friction coefficient) of the obtained sample was measured with the use of KES-SE friction tester (manufactured by Kato Tech Co., Ltd.). The measurement was performed at a friction measurement load of 25 gf, at a surface measurement sample moving speed of 1 mm/sec, and a measurement distance range of 20 mm. As a sensor, a silicone contact piece (a friction piece of silicone rubber with irregular shape assumed as a human finger) was used. As the value of MMD (mean deviation of friction coefficient) becomes smaller, the roughness of the obtained particle is less and the particle is very smooth.

BET specific surface area (m/g) in Table 1 is a value measured by using a fully automatic BET specific surface area measuring device Macsorb (manufactured by Mountech Co., Ltd.).

(Preparation of Coating Film 1)

In a mayonnaise bottle having a volume of 75 ml, 2 g of zinc oxide particles obtained in each of examples and comparative examples described above, 10 g of varnish (ACRYDIC A-801-P manufactured by DIC Corporation), 5 g of butyl acetate (special grade reagent, manufactured by Wako Pure Chemical Industries, Ltd.), 5 g of xylene (genuine special grade, manufactured by JUNSEI CHEMICAL CO., LTD.) and 38 g of glass beads (1.5 mm, manufactured by Potters-Ballotini Co., Ltd.) were put and sufficiently mixed, then fixed in a paint conditioner Model 5410 (manufactured by RED DEVIL, Inc.), and subjected to a dispersion treatment by giving vibrations for 90 minutes, thereby preparing a coating. Next, a small amount of the prepared coating was added dropwise onto a slide glass (length/width/thickness=76 mm/26 mm/0.8 to 1.0 mm, manufactured by Matsunami Glass Ind., Ltd.), and a coating film was prepared using a bar coater (No. 579 ROD No. 6, manufactured by YASUDA SEIKI SEISAKUSHO, LTD.). The prepared coating film was dried at 20° C. for 12 hours, and then used for measurement of total light transmittance 1, total light transmittance 2, parallel light transmittance 1, and parallel light transmittance 2.

(Total Light Transmittance 1, Total Light Transmittance 2, Parallel Light Transmittance 1 and Parallel Light Transmittance 2)

Herein, total light transmittance 1(%), total light transmittance 2(%), parallel light transmittance 1(%) and parallel light transmittance 2(%) are values obtained by measuring the prepared coating film using a spectrophotometer V-570 (manufactured by JASCO Corporation). The value of total light transmittance 1(%) is a value of total light transmittance at a wavelength of 310 nm, the value of total light transmittance 2(%) is a value of total light transmittance at a wavelength of 350 nm, the value of parallel light transmittance 1(%) is a value of parallel light transmittance at a wavelength of 500 nm, and the value of parallel light transmittance 2(%) is a value of parallel light transmittance at a wavelength of 700 nm. An ultraviolet blocking effect to ultraviolet rays having a wavelength of UVB is enhanced as the value of total light transmittance 1(%) becomes smaller, and an ultraviolet blocking effect to ultraviolet rays having a wavelength of UVA is enhanced as the values of total light transmittance 2(%) becomes smaller. Visible light transparency is enhanced as the values of parallel light transmittance 1(%) and parallel light transmittance 2(%) become larger.

(Preparation of Coating Film 2)

Sample 0.5 g and 0.8 g of KF-96-1000cs (manufactured by Shin-Etsu Chemical Co., Ltd.) were kneaded and rotated 50 times by using an automatic hoover muller for laboratory (manufactured by TOYO SEIKI SEISAKU-SHO Ltd.) at a rotation speed of 100 rpm and a load of 10 (lb), and the mixture was added dropwise onto a slide glass, and a coating film was prepared using a 1 mil applicator (manufactured by TOYO SEIKI SEISAKU-SHO Ltd.). The prepared coating film was used immediately after the preparation for measurement of total light transmittance 3(%), diffusing light transmittance (%), and haze (%).

(Haze)

The total light transmittance 3(%), diffusing light transmittance (%), and haze (%) of the coating film immediately after the preparation were measured by using a haze meter HM-150 (manufactured by MURAKAMI COLOR RESEARCH LABORATORY CO., Ltd.) and haze (%) was determined. Haze is a value calculated by a formula; diffusing light transmittance/total light transmittance 3×100

Large value of haze (%) means that soft focus effect (a so called effect of blurring a base) is enhanced, for example, that the particles are suitably used for a foundation of cosmetics. In addition, the measurement of total light transmittance is based on JIS K 7361, and the measurement of haze is based on JIS K 7136.

From Table 1 above, it is evident that the spherical zinc oxide particle consisting of integrated plate-like particles of the present disclosure have a sharp particle size distribution. Further, it is evident that the particle is a zinc oxide particle with a superior powder touch, a superior soft focus effect, and a high ultraviolet blocking property. Especially, it is clear that the spherical zinc oxide particles consisting of integrated plate-like particles of Examples 1 to 5 obtained by adding a hydrophilic dispersant during a neutralizing reaction have a more sharp particle size distribution than that of the indefinite-shaped zinc oxide particles consisting of integrated plate-like particles of Comparative Examples 1 and 2 obtained without using a hydrophilic dispersant during a neutralizing reaction, and show a superior powder touch and a superior soft focus effect caused by the specific shape. Further, it is evident that the above-mentioned particles of examples have a more sharp particle size distribution, and show a superior powder touch, a superior soft focus effect, and a higher ultraviolet blocking property relative to the indefinite-shaped zinc oxide particle of Comparative Example 3 having approximately the same median size as that of particles in examples.

INDUSTRIAL APPLICABILITY

The spherical zinc oxide particles consisting of integrated plate-like particles of the present disclosure can be used as a component of a cosmetic, a thermal conductive filler, and so on.

The invention claimed is:

1. Spherical zinc oxide particles consisting of integrated plate-like particles, which have a median size of 0.01 μm or more, a D90/D10 in particle size distribution of 5.0 or less and a BET specific surface area of 10 $m^2/g$ or more.

2. The spherical zinc oxide particle consisting of integrated plate-like particles according to claim 1, which is obtained by a method comprising a step (1) of neutralizing a zinc acetate aqueous solution by an alkali aqueous solution wherein said step (1) is performed in the presence of a hydrophilic nonionic dispersant having a HLB value of 10.0 to 20.

3. The spherical zinc oxide particles consisting of integrated plate-like particles according to claim 2, which have a MIU (average friction coefficient) of 1.0 or less.

4. The spherical zinc oxide particle consisting of integrated plate-like particles according to claim 3, which has a haze (%) of a coating film of 40% or more.

5. The spherical zinc oxide particle consisting of integrated plate-like particles according to claim 2, which has a haze (%) of a coating film of 40% or more.

6. A cosmetic comprising the spherical zinc oxide particle consisting of integrated plate-like particles according to claim 2.

7. A thermal conductive filler comprising the spherical zinc oxide particle consisting of integrated plate-like particles according to claim 2.

8. The spherical zinc oxide particles consisting of integrated plate-like particles according to claim 1, which have a MIU (average friction coefficient) of 1.0 or less.

9. The spherical zinc oxide particle consisting of integrated plate-like particles according to claim 8, which has a haze (%) of a coating film of 40% or more.

10. A method for producing the spherical zinc oxide particle consisting of integrated plate-like particles according to claim 8, which comprises a step (1) of neutralizing a zinc acetate salt aqueous solution by an alkali aqueous solution wherein said step (1) is performed in the presence of a hydrophilic nonionic dispersant having a HLB value of 10.0 to 20.

11. A cosmetic comprising the spherical zinc oxide particle consisting of integrated plate-like particles according to claim 8.

12. A thermal conductive filler comprising the spherical zinc oxide particle consisting of integrated plate-like particles according to claim 8.

13. The spherical zinc oxide particle consisting of integrated plate-like particles according to claim 1, which has a haze (%) of a coating film of 40% or more.

14. A method for producing the spherical zinc oxide particle consisting of integrated plate-like particles according to claim 13, which comprises a step (1) of neutralizing a zinc acetate aqueous solution by an alkali aqueous solution wherein said step (1) is performed in the presence of a hydrophilic nonionic dispersant having a HLB value of 10.0 to 20.

15. A cosmetic comprising the spherical zinc oxide particle consisting of integrated plate-like particles according to claim 13.

16. A thermal conductive filler comprising the spherical zinc oxide particle consisting of integrated plate-like particles according to claim 13.

17. A method for producing the spherical zinc oxide particle consisting of integrated plate-like particles according to claim 1, which comprises a step (1) of neutralizing a zinc acetate aqueous solution by an alkali aqueous solution wherein said step (1) is performed in the presence of a hydrophilic nonionic dispersant having a HLB value of 10.0 to 20.

18. A cosmetic comprising the spherical zinc oxide particle consisting of integrated plate-like particles according to claim 1.

19. A thermal conductive filler comprising the spherical zinc oxide particle consisting of integrated plate-like particles according to claim 1.

* * * * *